United States Patent [19]

Pinto et al.

[11] Patent Number: 5,703,301
[45] Date of Patent: Dec. 30, 1997

[54] UNIT DOSE BULK MATERIAL SAMPLING APPARATUS WITH CONTROLLED PRESSURE APPLICATOR

[75] Inventors: Ivan Pinto, West Chester, Pa.; Gerardo Perez, Elkton, Md.; Clarence W. Bowersox, Jr., West Chester, Pa.

[73] Assignee: Accutrol Company, Inc., West Chester, Pa.

[21] Appl. No.: 727,261

[22] Filed: Oct. 8, 1996

[51] Int. Cl.⁶ .................................................. G01N 1/00
[52] U.S. Cl. ............................................................. 73/864.63
[58] Field of Search ........................... 73/864.44, 864.45, 73/864.51, 864.62–864.64, 864.66, 864.67, 864.63

[56] References Cited

U.S. PATENT DOCUMENTS

| | | | |
|---|---|---|---|
| 4,866,996 | 9/1989 | Nohl et al. | 73/864 |
| 5,289,727 | 3/1994 | Earle et al. | 73/864.63 |
| 5,476,017 | 12/1995 | Pinto et al. | 73/864.63 |
| 5,492,021 | 2/1996 | Bourgeois et al. | 73/864.45 |

FOREIGN PATENT DOCUMENTS

0046450  1/1889  Germany ................ 73/864.63

*Primary Examiner*—Robert Raevis
*Attorney, Agent, or Firm*—Ratner & Prestia

[57] ABSTRACT

A sampler apparatus for unit dose bulk material sampling comprising an elongated housing having a first bore extending therethrough and a moveable piston rod extending through the first bore forming a sampling cavity between the front surface of the piston rod and the front end of the housing. A closure cap is attached to the front end of the housing and is adapted to selectively open and close the entrance to the sampling cavity. Also included are adjusting means for adjusting the size of the sampling cavity and compacting means for compacting the sample while the sample is contained within the sampling cavity.

12 Claims, 5 Drawing Sheets

UNIT DOSE BULK MATERIAL SAMPLING APPARATUS WITH CONTROLLED PRESSURE APPLICATOR

BACKGROUND OF THE INVENTION

1. Field of the Invention

This invention relates to a device for sampling bulk material. More particularly, this invention relates to a bulk material sampling device which can provide a controlled compaction force on the sample while the sample is contained within the device.

2. Description of Related Art

Sampling of bulk mixtures of granular or powdery materials to evaluate the degree of mixing at different locations in a mixing vessel is typically done using a probe or sample thief which is inserted in the bulk mixture to remove a representative sample therefrom. The probes generally comprise a long tubular shell having at least one aperture leading to a sampling cavity, either on a side wall near the lower end of the probe, or at the bottom of the probe. Further included is a means for opening the aperture to allow for bulk material to enter the sampling cavity, and a means for closing the aperture once the cavity is filled.

In operation, the probe is inserted in the bulk mixture to the desired depth, with the aperture closed. After insertion of the tube to a desired depth, the aperture is opened, thus exposing the cavity and allowing bulk material to enter the cavity. The opening is then closed and the probe is removed from the bulk material retrieving a sample of the material from a desired point in the mixing vessel. The sample retrieved is recovered from the probe for further analysis or study as needed.

Generally, such bulk sampling apparatus are satisfactory for collecting samples, however, these apparatus suffer from an inability to sample an accurate and representative sample of the bulk material. This is the result of the lack of control over the amount of material that is collected and separation/segregation of the material during sampling, thus prohibiting the capturing of an accurate and repeatable sample to be obtained and tested. In particular, when collecting powdery samples, as is frequently the case for pharmaceutical applications, the recovered sample represents a unit dose corresponding to a particular medicinal pill composition. As such, it is essential that all of the sample contained in the cavity be recovered. It is preferred, in such instances, that compaction of the sample take place prior to discharge of the sample from the cavity. Compaction is desirable because dispensing non-compacted powdery material results in losses of the material due to the powder being carried away in an airstream as it flows from the cavity to the sample holder, and while the sample is in the sample holder for analysis.

An improved sampling device is disclosed in recently issued U.S. Pat. No. 5,476,017, issued to Pinto et al., which is herein incorporated by reference. This patent discloses a bulk sampling device which has the ability to recover predetermined sized samples with a high degree of repeatability. The device works by filling the sampling cavity from the bottom, thus allowing for the capture of much more consistently sized samples. In particular, a sampling probe is fed into the bulk material while the sampling cavity is closed. The front end of the probe is rotated in such a way to expose the sampling cavity. The probe is then pushed further into the bulk material forcing bulk material into the sampling cavity. The cavity is then closed by returning the front end of the probe back into its closed position, and the probe is removed from the material.

Once the probe is removed from the bulk material, the powdery material within the sampling cavity is compacted. In particular, the probe is positioned substantially perpendicular to the ground with the front end down. While the probe is held in this position, a small mallet or other similar instrument is used to apply a compacting force onto a piston which is positioned over the sample, forcing the piston down upon the sample, and thus compacting the sample within the cavity. Although this compacting means may be effective, it is uncontrolled and very inconsistent in terms of the amount of pressure being placed on each sample each time.

Thus there is a need for a bulk sampling apparatus which provides a simple controlled and consistent compaction force on each sample prior to the ejection of the sample from the sampling cavity of the apparatus.

These and other objects of the present invention will be clear from the following description.

SUMMARY OF THE INVENTION

In accordance with the present invention there is provided a sampler apparatus for unit dose bulk material sampling, comprising:

- an elongated housing having a length, an axis coextensive with said length, a first bore extending in the direction of said axis the length of said housing, a front end having a front opening aligned with said first bore, said front end and front opening lying in a plane substantially perpendicular to the axis, and a back end;

- a moveable piston rod supported in said first bore, comprising a front surface in a plane perpendicular to the axis and a shaft extending from said front surface in a direction opposite said front surface in the direction of said axis, the front surface having a diameter substantially equivalent to the diameter of the first bore;

- a sampling cavity formed within the first bore and extending between the front surface of the piston rod and the front end of the housing, wherein the front opening of the front end of the housing forms an entrance to the sampling cavity;

- adjusting means for selectively varying the position of the front surface of the piston in the first bore for adjusting, presetting, and locking the size of the sampling cavity;

- a closure cap attached to said housing and having means for selectively controlling opening and closing said entrance to the sampling cavity; and

- a compacting means for moving said moveable piston rod a predetermined distance in the direction of said axis whereby the sampling cavity is reduced in size by a predetermined amount.

BRIEF DESCRIPTION OF THE DRAWINGS

The invention can be more fully understood from the following description thereof in connection with the accompanying drawings described as follows.

DESCRIPTION OF THE PREFERRED EMBODIMENT(S)

Throughout the following detailed description, similar reference characters refer to similar elements in all figures of the drawings.

The crux of this invention relates to the ability of the sampling apparatus to consistently and repeatedly apply the same compacting force on each sample that is retrieved by the sampling device. The compaction pressure is applied to the sample while the sample is still contained within the sampling cavity of the device. As such, equivalent sized samples of a predetermined size can be consistently recovered from the apparatus.

Figure 1:
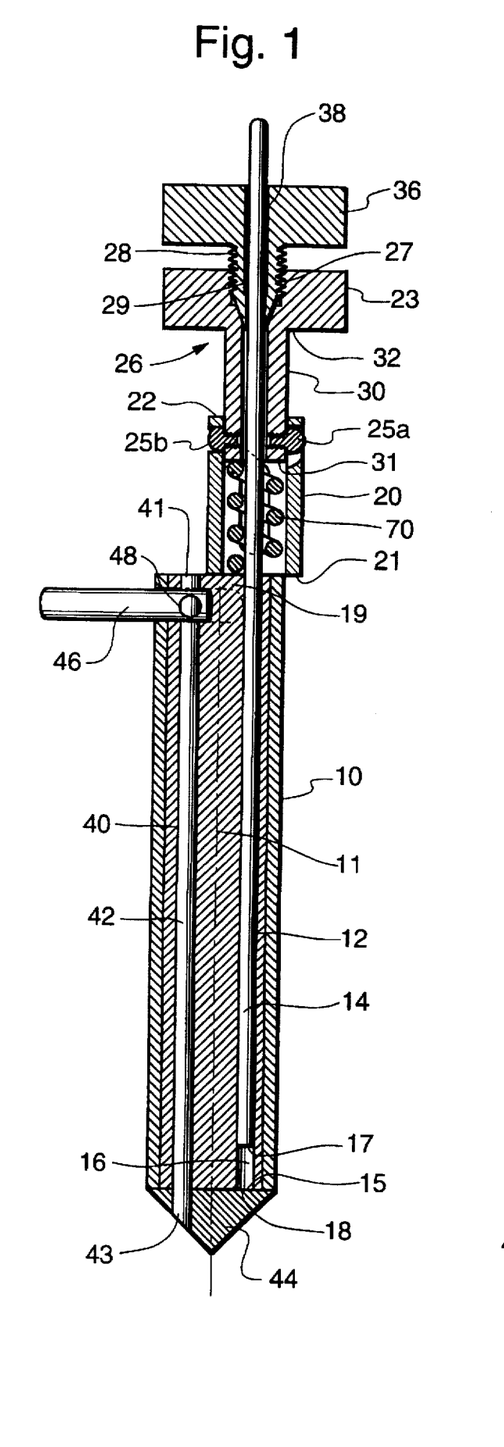
FIG. 1 is a schematic cross-sectional elevation view of one embodiment of the present device showing the closure cap in the closed position.
Figure 2:
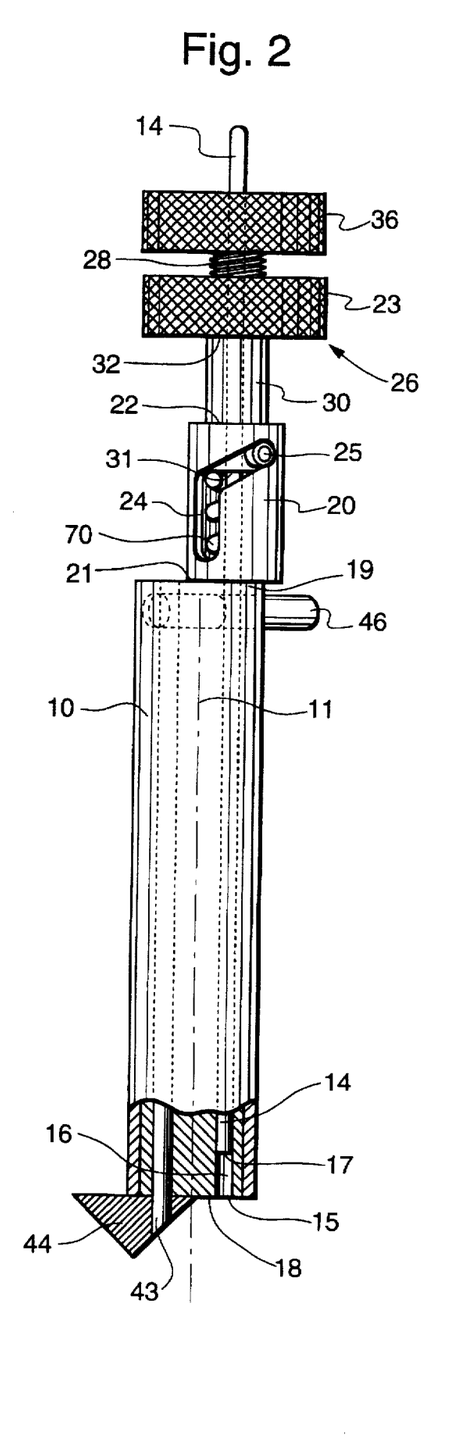
FIG. 2 is a schematic representation of an elevation view of one embodiment of the present device showing the closure cap in the open position.

Referring now to FIGS. 1 and 2 there is shown an apparatus in accordance with this invention. The apparatus, referred to hereinafter as the "probe" comprises an elongated housing 10 which is preferably cylindrical in shape and having an axis 11 extending along the long dimension of the housing 10. The housing 10 is preferably solid and has first and second bores 12, 40 extending therethrough. Both the first and second bores 12, 40 are preferably cylindrical and lie parallel to axis 11 of housing 10. Housing 10 has a front end 18 and a back end 19.

Front end 18 has a front opening or entrance 15 aligned with first bore 12 wherein the entrance 15 is generally contained in a plane perpendicular to axis 11.

Attached to the back end of housing 10 is a sleeve 20. Sleeve 20 has a front end 21 and a back end 22, and is preferably elongated, cylindrical in shape, and hollow. Sleeve 20 includes at least one groove 24 in which rides at least one corresponding cam 25, as best seen in FIG. 2. More detail on sleeve 20 and its associated parts will be given later in this description.

Partially contained within sleeve 20 is neck portion 30. The front end 31 of neck portion 30 is contained within sleeve 20 while the back end 32 of neck portion 30 extends out past the back end 22 of sleeve 20. Cam 25 is preferably attached near the front end of neck portion 30 (within sleeve 20) and is aligned with and protrudes through groove 24. More detail on the neck portion 30 and its interrelationship with sleeve 20 will be given later in this description.

The back end 32 of neck portion 30 is connected to a compacting knob 23. Neck portion 30 and compacting knob 23 together form a cam follower 26. Compacting knob 23 is preferably cylindrically shaped and preferably has a threaded bore 27 formed within it. Contained within threaded bore 27 is threaded portion 28. Threaded portion 28 includes a longitudinal bore 29 having a diameter approximately equivalent to first bore 12 of housing 10. Bore 29 runs in the direction of axis 11 and is preferably aligned with first bore 12.

Preferably, the front end of threaded portion 28 is threaded into threaded bore 27 as shown in FIG. 1. The back end of threaded portion 28 is preferably fixedly attached to knob 36 which is used for adjusting the size of sampling cavity 16, as will be explained momentarily. Knob 36 is generally solid but includes a longitudinal bore 38 aligned with bore 29 of threaded portion 28 and has a diameter approximately equivalent to the diameter of bore 12 of housing 10.

As seen in FIG. 1, bores 29 and 38 must be aligned with bore 12 of housing 10 to form a continuous bore. Disposed within and extending through bores 12, 29 and 38 is piston rod 14. Piston rod 14 also extends through sleeve 20 and neck portion 30.

Piston rod 14 extends through knob bore 38 above adjusting knob 36. Knob 36 has a threaded tapered lower end 28 which is shaped like a collet. Threaded end 28 is screwed into bore 27 to secure or release piston rod 14. The cavity size is adjusted by unscrewing knob 36, thus releasing the piston, moving the piston to a new position and then screwing the knob back into compacting knob 23 to tighten its grip on the rod 14 and secure it in position. In a preferred embodiment shown in FIG. 3, adjusting knob 36 and cam follower knob 23 may incorporate a collet 39 for locking the piston rod 14 at the desired sample size. In particular, once the bore size has been adjusted by moving piston rod 14 up or down, adjusting knob 36 is turned and collet 39 is compressed around piston rod 14 to lock it in place.

Piston rod 14 ends in a front surface 17 which lies in a plane perpendicular to the axis 11. The front surface 17, the inside walls of bore 12 and the front end 18 of housing 10 define sampling cavity 16 whose total volume is varied by moving the rod 14 along axis 11 as described above.

Typical cavity volumes for unit dose sampling as used by the Pharmaceutical industry are in the range of 1 to 5 cubic centimeters. However, these dimensions are illustrative rather than limiting and a probe built in accordance with the present invention may provide cavity sizes substantially different than those mentioned, the cavity size depending primarily on the application and sample size.

Piston rod 14 rides within bore 12 of housing 10 in the direction of axis 11. In one embodiment shown in FIG. 1, the rod 14 is sized to completely fit inside bore 12 so that the rod 14 wipes the inside of bore 12 as it moves in the direction of axis 11.

Figure 5:
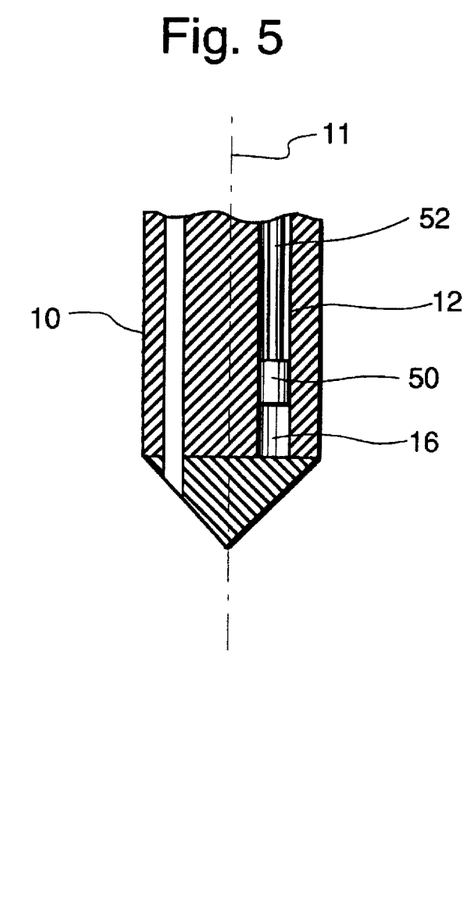
FIG. 5 is a cross-sectional elevation view of the an alternate embodiment of the moveable piston rod of the present device.

An alternate embodiment is shown in FIG. 5 wherein piston rod 14 comprises a plug 50 and a shaft 52 extending from the plug 50. In this embodiment, only the plug 50 is sized to completely fit inside bore 12 so that the plug 50 wipes the inside of the bore as it moves in the direction of axis 11.

Both the sleeve 20 and neck portion 30 are hollow cylinders. The diameter of each of the sleeve 20 and neck portion 30 are greater than the diameter of piston rod 14. It is important that piston rod 14 be able to freely move up and down along axis 11 and rotate about its axis within sleeve 20 and neck portion 30 (see FIG. 1).

A spring 70 is disposed within sleeve 20. Spring 70 is disposed between the back end 19 of housing 10 and the front end 31 of neck portion 30. The purpose of spring 70 is to keep neck portion 30 biased towards the back end of sleeve 20. Neck portion 30 is kept partially contained within the sleeve 20 by the utilization of cams 25a and 25b and corresponding grooves 24a and 24b. More than one spring and other biasing means including hydraulics can be used in the invention.

Figure 6A:
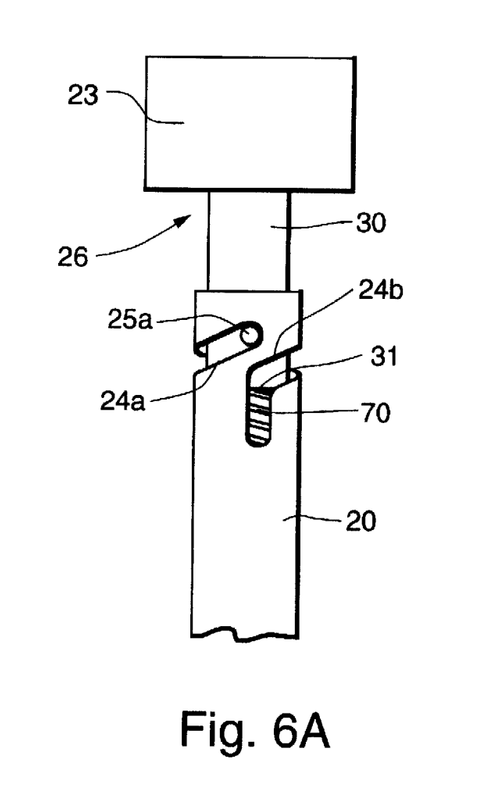
FIG. 6a shows one embodiment of the sleeve, cam and cam follower portion of the present device wherein these portions are in the first, sampling position.
Figure 6B:
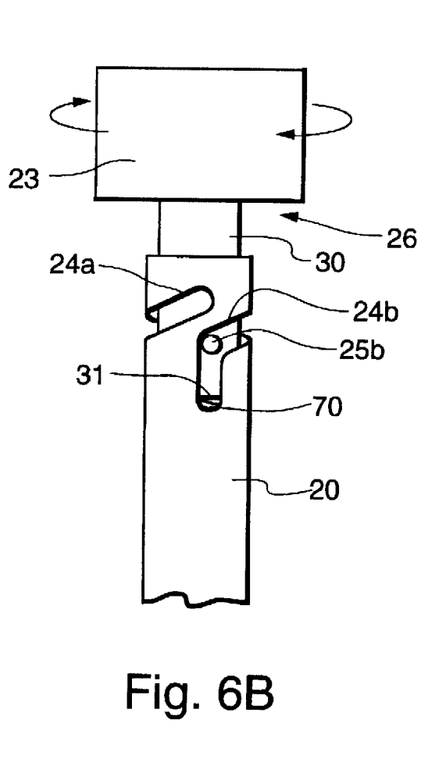
FIG. 6b shows one embodiment of the sleeve, cam and cam follower portion of the present device wherein these portions are in the second, compacting position.
Figure 6C:
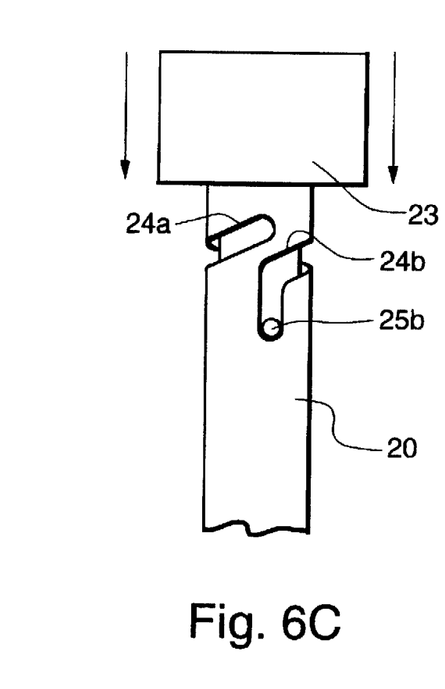
FIG. 6c shows one embodiment of the sleeve, cam and cam follower portion of the present device wherein these portions are in the third, ejection position.

FIGS. 6a, 6b, and 6c show sleeve 20, neck portion 30 and compacting knob 23 in their three primary positions. In FIG. 6a, sleeve 20, neck portion 30 and compacting knob 23 are in the first, biased sampling position whereby the neck portion 30 is nearly completely outside of sleeve 20, due to the biasing action of spring 70. As is seen in the figure, cam 25a rests at the back end of groove 24a. It is preferred that there be a second cam 25b (only shown in FIG. 6b) disposed 180 degrees around neck portion 30 from cam 25a. Cam 25b is disposed within its corresponding groove 24b. The adjustment of the size of sampling cavity 16 is accomplished while cams 25a and 25b are in this sampling position.

FIG. 6b shows sleeve 20, neck portion 30 and compacting knob 23 in the second, compacting position. Arrows are pictured in FIG. 6b to show how compacting knob 23 is turned in order compact the sample. As compacting knob 23 is turned, cams 25a and 25b move along the path of grooves 24a and 24b respectively until the compacting position shown in FIG. 6 is reached. Because cam follower 26 is attached to piston rod 14 through adjusting knob 36 and threaded portion 28, as compacting knob 23 is turned, piston rod 14 is driven towards the front end 18 of housing 10 thus reducing the area of sampling cavity 16. Of course, when sample is contained within sampling cavity 16, rotating of the cam follower 26 will compact the sample within the sampling cavity by a predetermined amount.

Due to the shape and path of grooves 24a and 24b, each time cam follower 26 is turned from the sampling position to the compacting position (i.e. cam 25 follows the incline plane of groove 24), piston rod 14 applies the same amount of pressure on each sample within cavity 16. As such, each recovered sample, upon ejection from the probe, will be compacted by the same, predetermined amount, thus allowing the probe user to recover a similar sample each time. As stated in the background, this is extremely important, for instance, in the Pharmaceutical industry, where powdery materials are collected in amounts that represent unit doses. In such a case, it is necessary that all of the material be recovered from the sampling cavity. Note: pressure does not determine sample size, nor does compacting pressure vary with the sample size.

FIG. 6c shows sleeve 20, neck portion 30 and compacting knob 23 in the final, ejection position. Once the cam follower 26 is turned to the second, compacting position, the cams 25a and 25b are in position in their corresponding grooves 24a and 24b to move directly downwards, toward front end 21 of sleeve 20. At this point, in order for the sample to be ejected, the cap 44 located at the front end 18 of housing 10 is moved away from entrance 15 to expose cavity 16. Arrows are pictured in FIG. 6c to show the movement of compacting knob 23 in order to effectuate the downward movement of the piston rod 14 needed to eject the sample from the cavity 16. Pressure is placed on compacting knob 23 in the direction of the arrows shown in the figure and the sample will be ejected.

Figure 7:
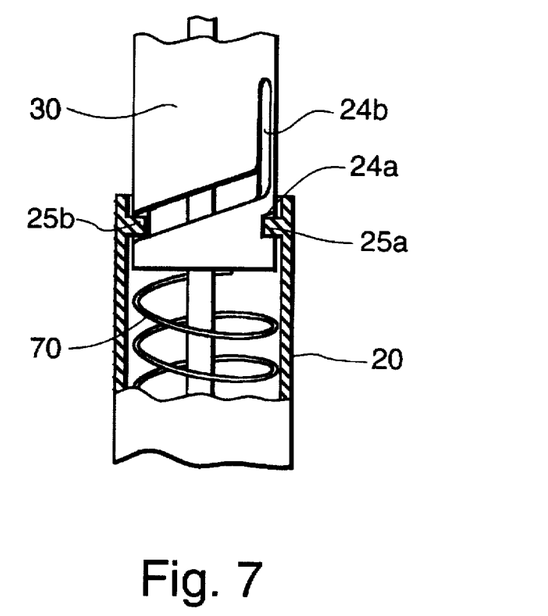
FIG. 7 is a schematic representation of an elevation view of an alternate embodiment of the cam and sleeve of the present device.

An alternate embodiment of sleeve 20 and neck portion 30 is shown in FIG. 7 wherein sleeve 20 and neck portion 30 are designed in the reverse of that described above. In particular, cams 25a and 25b are attached to and protrude inwardly from the inside of sleeve 20 into grooves 24a and 24b on neck portion 30. Nevertheless, the first, sampling, second, compacting and third, ejection positions of the sleeve 20 and piston rod 14 are attained in the same manner as described above.

Referring back again to FIG. 1, there is shown second bore 40. As briefly described earlier, second bore 40 is preferably cylindrical and lies coaxially with the housing 10 along axis 11. Disposed within and extending throughout second bore 40 is cap shaft 42. Cap shaft 42 extends from the back end 19 of housing 10 through the front end 18 of housing 10. Second bore 40 is open at the front end 18 thus allowing the front end 43 of shaft 42 to extend through it, past the front end 18 of housing 10. Shaft 42 is disposed within second bore 40 in such a way that it is free to rotate around its axis within the bore 40, but cannot move axially.

Front end 43 of shaft 42 preferably extends into and is fixedly attached to a closure cap 44. Closure cap 44 is preferably frusto-conically shaped, having a pointed end and a base, and is mounted near the front end 18 of housing 10. Closure cap 44 is preferably mounted to the housing 10 via its connection to shaft 42.

Closure cap 44 is positioned such that when it is in the closed position as shown in FIG. 1, the entrance to sampling cavity 16 is closed. Cap 44 is moved from the closed position to the open position shown in FIG. 2 through the action of shaft 42. It is preferred that shaft 42 be rotated such that cap 44 is rotated away from front end 18 of housing 10, thus exposing entrance 15 to sampling cavity 16 (best seen in FIG. 2).

Figure 3:
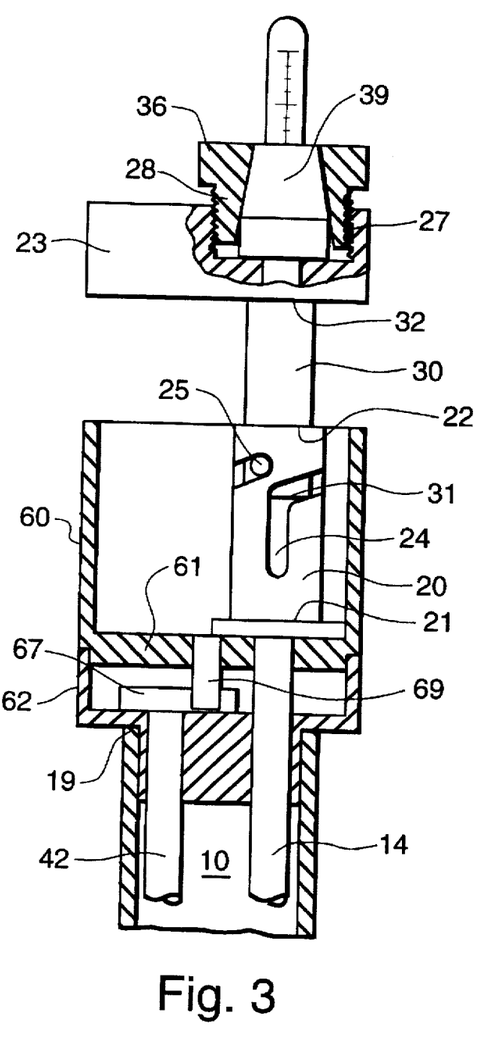
FIG. 3 is a schematic cross-sectional elevation view of one embodiment of the back end of the apparatus.
Figure 4:
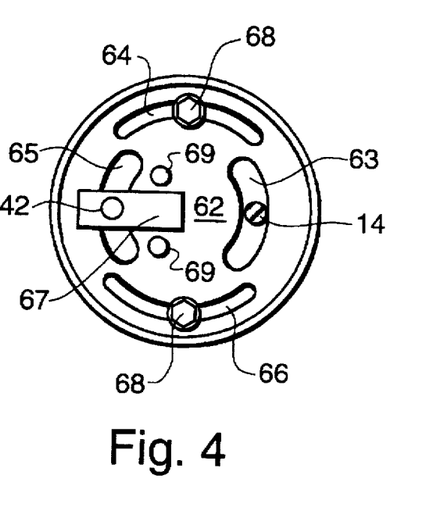
FIG. 4 is an overhead view of the base connected to the top end of the housing.

In a preferred embodiment shown in FIGS. 3 and 4, closure cap 44 is rotated from the open to closed position and vice versa through a hollow closure cap knob 60. Hollow closure cap knob 60 surrounds sleeve 20 as shown in FIG. 3. Closure cap knob 60 includes a bottom 61 which is rotatably mounted onto a base 62. Base 62 is fixedly mounted onto top end 19 of housing 10.

Now referring specifically to FIG. 4, base 62 preferably includes four slots 63–66. Slots 63 and 65 provide the openings through which piston rod 14 and cap shaft 42 extend through, while slots 64 and 66 provide openings through which shoulder screws 68 extend through. Shoulder screws 68 are fixedly attached at one end to the base 62. The head of the screw 68 rests on the top surface of bottom 61 of knob 60 and is used to rotatably hold knob 60 against the base 62. The slots 63–66 allow for the rotation of knob 60 while not forcing the piston rod 14 or the cap shaft 42 to move with it.

In order to effectuate the rotation of cap shaft 42, knob 60 preferably also includes two pins 69 which extend from the bottom 61 of knob 60 but do not extend as far as the base 62. The pins 69 are disposed on either side of one end of an internal handle 67. The opposite end of internal handle 67 is fixedly attached to the back end 41 of shaft 42. As such, when knob 60 is rotated, pins 69 push the internal handle, forcing shaft 42 to rotate. The rotation of shaft 42 results in the rotation of closure cap 44 from the open to closed position, and vice versa.

In an alternate embodiment shown in FIG. 1, an external handle 46 is connected to the back end 41 of shaft 42 in order to effectuate the turning of shaft 42. Preferably, the orientation of handle 46 is such as to indicate at a glance whether the closure cap 44 is in the open or closed position. This may be readily done by aligning the handle along a line extending from the shaft 42 axis in the base of closure cap 44 to a point representing the projection of the apex of the cap 44 onto the base. Other indicating arrangements may of course be used. In addition, other modes of effectuating the turning of shaft 42 are contemplated and include the use of a lever, switch, or any other applicable means, such as a internal lever moved with cam pins.

Figure 8:
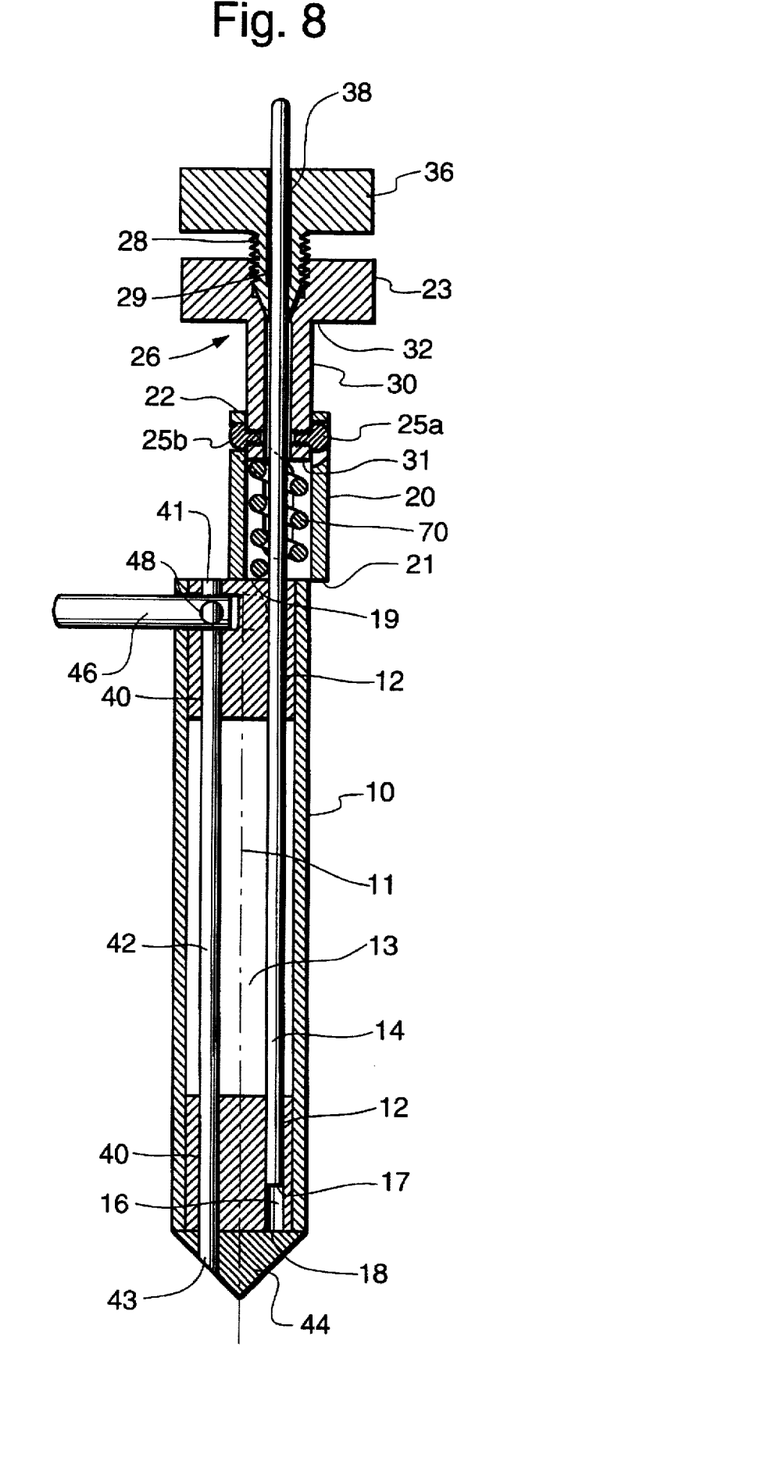
FIG. 8 is a schematic cross-sectional elevation view of an alternate embodiment of the present device showing the closure cap in the closed position.

An alternate embodiment of the housing is shown in FIG. 8. Included in this embodiment is a large bore 13 formed within housing 10. As such, bores 12 and 40 do not extend the full length of housing 10, but are merely formed at the front and back ends 18, 19 of the housing 10 as seen in the figure. The bores 12 and 40 formed at the front end 18 of the housing must be aligned with their counterparts at the back end 19 in order for piston rod 14 and cap shaft 42 to fit axially within them respectively and extend through the housing. The purpose of such an embodiment is to save on costs, materials and to reduce the weight of the device.

In operation, a probe constructed according to this invention is first adjusted to remove a predetermined sample size from the bulk material for testing. The size of sampling cavity 16 is adjusted for a particular sized sample by rotating adjusting knob 36, to release the grip on piston rod 14, then moving rod 14 to the desired position using the markings on the portion of the rod extending above knob 36 and finally retightening the knob 36. The adjustment may be based on pre-established, calibrated settings marked on the rod, or may be done by trial and error by measuring the contents of the cavity 16 and further adjusting the position of piston rod 14 to obtain the desired volume.

Once the desired volume of cavity 16 has been established, the closure cap 44 is placed in the closed position, sealing the entrance 15 to cavity 16. The probe is then inserted into the bulk material to a desired depth from which a sample of the material is to be obtained. When the proper insertion point has been reached, the closure cap 44 is rotated by rotating knob 60 such that closure cap 44 rotates completely away from the entrance to cavity 16, thus exposing cavity 16. The probe is then pushed further into the bulk material by a small distance forcing bulk material into cavity 16 through the open front entrance. The closure cap is then closed, sealing the cavity with the sample enclosed, and the probe is removed from the bulk material.

Once the probe is removed from the bulk material, the next step depends on what type of material is being sampled. When sampling powdery substances such as those often used for pharmaceutical applications, the sample represents a unit dose corresponding to a particular medicinal pill composition. As such, it is essential that all of the sample in the cavity be recovered if any accurate analysis of the degree of component mixing in the sampling vicinity is to be obtained. In such cases, the amount typically sampled is very small, and even a small loss of material produces a large, proportionate error in the sampling process. As such, it is preferred that compaction of the sample prior to discharging the sample from the cavity take place.

To properly recover all of the material from the sampling cavity, the probe is stood up substantially perpendicular to the ground with the closure cap tip pointing to the ground. Compacting knob 23 is turned such that cams 25a and b move through respective grooves 24a and b from the first sampling position to the second compaction position. Due to the angle of the grooves, the turning of compacting knob 23 forces piston rod 14 to move towards the front end of the housing, thus compacting the powdered substance contained within the cavity. The compacting of the powdery substance will form a pellet. This compacting force will be the same for every sample tested for that sized cavity. As such, the resulting pellets are highly repeatable and permit a very accurate analysis of the degree of component mixing in the sampling vicinity.

Once the sample has been compressed into a pellet, the closure cap is rotated to expose entrance 15 of cavity 16. At that point, compacting knob 23 is moved from the second, compacting position to the third, ejection position. This is accomplished by applying pressure in the longitudinal direction of the probe as depicted in FIG. 6c. This final push ejects the compacted pellet completely out of the cavity without leaving any of the sample behind in the cavity.

In pharmaceutical applications, because of the ability to consistently compress each sample and thus consistently empty the sampling cavity, and because of the ability to test the compacted sample material without substantial further sample losses in the handling of the pelletized sample, the sample size can be adjusted with sufficient accuracy so that each compacted pellet represents an equivalent single dose of a particular medication sampled.

All parts of this apparatus can be made from any solid material which can hold up to the pressure of being inserted into the bulk material. Some examples of materials which can be used preferably include stainless steel.

Those skilled in the art having the benefit of the teachings of the present invention as hereinabove set forth, can effect numerous modifications thereto. These modifications are to be construed as being encompassed within the scope of the present invention as set forth in the appended claims.

I claim:

1. A sampler apparatus for unit dose bulk material sampling, comprising:

an elongated housing having a length, an axis coextensive with said length, a first bore extending in the direction of said axis the length of said housing, a from end having a front opening aligned with said first bore, said front end and front opening lying in a plane substantially perpendicular to the axis, and a back end;

a moveable piston rod supported in said first bore, comprising a front surface in a plane perpendicular to the axis and a shaft extending from said front surface in a direction opposite said front surface in the direction of said axis, the front surface having a diameter substantially equivalent to the diameter of the first bore;

a sampling cavity formed within the first bore and extending between the from surface of the piston rod and the front end of the housing, wherein the front opening of the front end of the housing forms an entrance to the sampling cavity;

adjusting means for selectively varying the position of the front surface of the piston in the first bore for adjusting, presetting, and locking the size of the sampling cavity;

a closure cap attached to said housing and having means for selectively controlling opening and closing said entrance to the sampling cavity; and a cam follower connected to the piston rod, for moving said moveable piston rod a predetermined distance in the direction of said axis whereby the sampling cavity is reduced in size by a predetermined amount, said cam follower comprising:

a neck portion having at least one cam attached thereto; and a compacting knob.

2. The sampler apparatus of claim 1 further comprising a sleeve connected to the housing, the sleeve comprising a hollow cylindrical tube having a groove, wherein the neck portion is partially disposed within the sleeve and the cam rides in the groove.

3. The sampler apparatus of claim 2 further comprising a biasing means disposed between the back end of the housing and the neck portion.

4. The sampler apparatus of claim 3 wherein the biasing means is disposed within the sleeve.

5. The sampler apparatus of claim 4 wherein the biasing means comprises a spring.

6. The sampler apparatus of claim 2 wherein the compacting means moves the moveable piston rod from a first, sampling position, to a second, preset, compacting position.

7. The sampler apparatus of claim 6 wherein the adjusting means comprises an adjusting knob rotatably associated with the compacting knob and fixedly connected to the moveable piston rod.

8. The sample apparatus of claim 6 wherein the adjusting means includes a collet.

9. The sampler apparatus of claim 1 wherein the closure cap is rotatably attached to the housing.

10. The sampler apparatus of claim 10 wherein the means for opening and closing the entrance to the sampling cavity comprises a second bore extending in the direction of the axis of the housing, wherein a cap shaft, having a front end and a back end, extends through the second bore in the direction of the axis of the housing, said cap shaft adapted to rotate around its axis and wherein the front end of the cap shaft extends out of the front end of the housing and is attached to the closure cap.

11. The sampler apparatus of claim 10 further comprising a knob disposed at the back end of the housing and connected to the back end of the cap shaft, the knob adapted to rotate the shaft around its axis.

12. The sampler apparatus of claim 10 further comprising a handle connected to the back end of the cap shaft for rotating the shaft around its axis, said handle extending substantially perpendicular to the axis of the housing.

* * * * *

UNITED STATES PATENT AND TRADEMARK OFFICE
CERTIFICATE OF CORRECTION

PATENT NO. : 5,703,301

DATED : December 30, 1997

INVENTOR(S) : Ivan Pinto, Gerardo Perez, Clarence W. Bowersox, Jr.

It is certified that error appears in the above-identified patent and that said Letters Patent are hereby corrected as shown below:

In claim 1, on column 8, line 31, replace "from" with: --front--.

In claim 1, on column 8, line 42, replace "from" with: --front--.

In claim 10, on column 9, line 16, replace "10" with: --9--.

Signed and Sealed this

Third Day of March, 1998

Attest:

BRUCE LEHMAN

Attesting Officer

Commissioner of Patents and Trademarks